United States Patent [19]

Takase et al.

[11] Patent Number: 5,685,825
[45] Date of Patent: Nov. 11, 1997

[54] ENDOSCOPE

[75] Inventors: Seisuke Takase; Tetsuaki Mori; Akihiro Okubo; Yasushi Machida, all of Hachioji, Japan

[73] Assignee: Olympus Optical Co., Ltd., Tokyo, Japan

[21] Appl. No.: 576,779

[22] Filed: Dec. 21, 1995

[30] Foreign Application Priority Data

Mar. 3, 1995 [JP] Japan ................................. 7-044347

[51] Int. Cl.$^6$ ................................. A61B 1/005
[52] U.S. Cl. ................ 600/140; 600/101; 600/121; 600/133; 600/139; 604/158; 604/265; 604/266; 528/59; 528/80
[58] Field of Search ................. 128/4; 604/158, 604/265, 266; 600/101, 121, 133, 140, 139; 528/59, 80

[56] References Cited

U.S. PATENT DOCUMENTS

| | | | |
|---|---|---|---|
| 4,003,382 | 1/1977 | Dyke | 128/348 |
| 4,523,005 | 6/1985 | Szycher | 528/76 |
| 4,805,596 | 2/1989 | Hatori | 128/4 |
| 5,045,072 | 9/1991 | Castillo et al. | 604/280 |
| 5,127,393 | 7/1992 | McFarlin et al. | 128/4 |
| 5,135,516 | 8/1992 | Sahatjian et al. | 604/265 |
| 5,170,775 | 12/1992 | Tagami | 128/4 |
| 5,171,232 | 12/1992 | Castillo et al. | 604/280 |
| 5,385,152 | 1/1995 | Abele et al. | 128/772 |
| 5,441,489 | 8/1995 | Utsumi et al. | 604/280 |
| 5,443,907 | 8/1995 | Slaikeu et al. | 428/375 |
| 5,545,151 | 8/1996 | O'Connor et al. | 604/282 |

FOREIGN PATENT DOCUMENTS 2-283346  11/1990  Japan .

*Primary Examiner*—Rabon Sergent
*Attorney, Agent, or Firm*—Frishauf, Holtz, Goodman, Langer & Chick, P.C.

[57] ABSTRACT

An endoscope comprising a flexible tubular body characterized in that a coating layer of aliphatic resins is formed on at least one surface of the outermost layer portion of the flexible tubular body. The coating layer of aliphatic resins is formed by applying a coating agent containing an aliphatic prepolymer on the surface, followed by curing.

18 Claims, 1 Drawing Sheet

ENDOSCOPE

BACKGROUND OF THE INVENTION

1. Field of the Invention

The present invention relates to an endoscope comprising a flexible tubular body, and more particularly, to an endoscope comprising a flexible tubular body excellent in chemical resistance.

2. Description of the Related Art

An endoscope such as a medical endoscope has to be inserted deeply into a body cavity, for example, the duodenum, small intestine, and large intestine. To insert the endoscope smoothly while mitigating patient's pain, the insertion section of the endoscope is required to be made of a flexible resin. Furthermore, to use the endoscope repeatedly, the insertion section has to be disinfected whenever it is used. It is therefore required that the insertion section be made of a material excellent in chemical resistance.

An endoscope whose insertion section satisfies the requirements mentioned above is disclosed in Jpn. Pat. Appln. KOKAI Publication No. 2-283346. The insertion section of the endoscope has a sheath consisting of two layers. The inner layer is made of a polyester resin superior in volatility. The outer layer is made of a polyurethane resin superior in chemical resistance and wear resistance.

Hitherto, glutaraldehyde disinfectants have been mostly used as a disinfectant for a conventional endoscope. Therefore, the insertion section of the conventional endoscope has been made of a material highly resistant to the glutaraldehyde disinfectants. However, the glutaraldehyde disinfectants have the drawbacks in that they need a long time to complete a disinfecting treatment and emits strong odor in the environment. To overcome these drawbacks, improvement of the glutaraldehyde disinfectants has been strongly desired.

In place of the glutaraldehyde disinfectants, various disinfectants have recently come to use. Among them, oxidative disinfectants such as hydrogen peroxide and highly concentrated acetic acid are used most frequently in the disinfectant market. However, the insertion section of the endoscope disclosed in Jpn. Pat. Appln. KOKAI Publication No. 2-283346, is not fully resistant to the oxidative disinfectants.

To impart sufficient chemical resistance to the insertion section, researchers have devised to coat the outer surface of the insertion section with an aromatic coating agent. The coating layer thus formed certainly exhibits high resistance to conventional disinfectants but not fully resistant to the oxidative disinfectants.

When an endoscope is disinfected, the light guide cable is inevitably exposed to the disinfectant. Hence, the light guide cable, as well as the insertion section into a body cavity must be fully chemical resistant.

SUMMARY OF THE INVENTION

The present invention has been made under the aforementioned circumstances to provide an endoscope having a tubular body having excellent chemical resistance to oxidative disinfectants.

According to the present invention, there is provided an endoscope comprising a flexible tubular body, wherein at least one portion of the flexible tubular body has a coating layer of aliphatic resins which is formed by applying a coating agent containing an aliphatic prepolymer onto the surface of an outermost layer, and curing the coating agent.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

DETAILED DESCRIPTION OF THE PREFERRED EMBODIMENTS

In the endoscope of the present invention, a coating layer of aliphatic resins, which is formed by applying an aliphatic prepolymer followed by curing, is formed to an outer surface of a tubular body. The coating layer of aliphatic resins thus formed attains not only a smooth surface but also an excellent chemical resistance to oxidative disinfectants which have been frequently used in recent years. Even if an oxidative disinfectant is applied onto the tubular body covered with such a coating layer of aliphatic resins, the surface of the tubular body will not lose its smoothness and maintain the same appearance.

Hereinbelow, embodiments of the present invention will be described with reference to the drawings.

Figure 1:
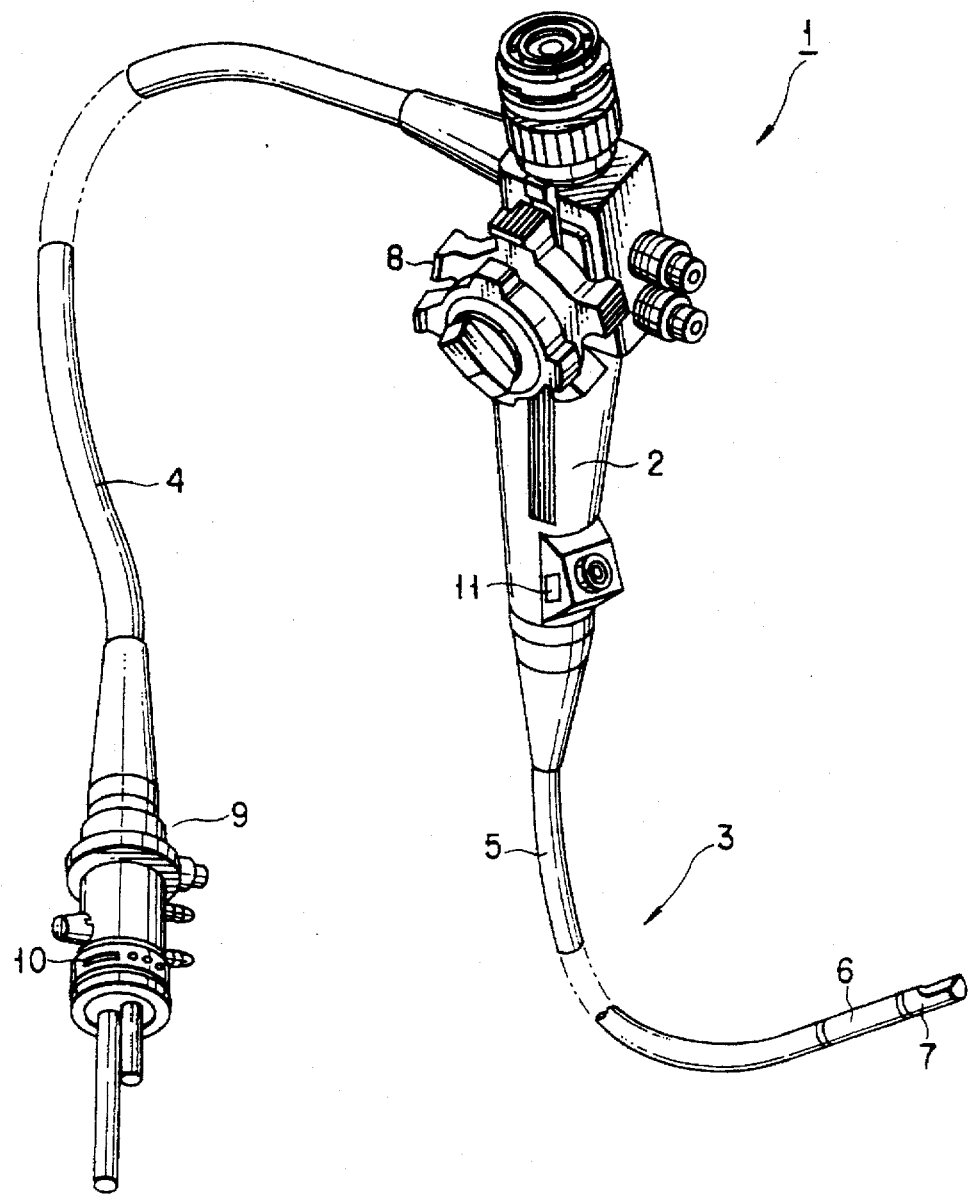
FIG. 1 is an overall view of an endoscope according to an embodiment of the present invention.

FIG. 1 shows an overall view of an endoscope according to an embodiment of the present invention. An endoscope 1 includes a control section 2, an insertion tubular section 3 formed of a flexible tubular material, and a light guide cable 4 formed of a flexible tubular material. The insertion tubular section 3 comprises, in the order from the control section 2, a flexible tube 5, the bending section 6 and a distal section 7. The flexible tube 5 is connected to the bending section 6 via connecting section (not shown). The bending section 6 is operated, so as to bend in a predetermined direction, through remote control by a bending operation knob 8 attached to the control section 2.

In one aspect of the present invention, a coating layer is formed on at least one surface of the portion selected from the group consisting of the flexible tube 5, a bending section 6 of the insertion tubular section 3, and the connecting section therebetween (not shown). In the case where the coating layer is formed on the surfaces of two portions or more, the coating material may be the same or different. Although the thickness of the coating layer is not particularly restricted, it is preferred to fall within the range between about 0.005 to 0.1 mm.

An end of the light guide cable 4 is connected to a connecter portion 9 which is connected to a light source apparatus (not shown). To the connector portion 9, equipped is a display board 10 indicating a manufacture number of the endoscope 1. It is preferred that the display board 10 be made of a stainless material to ensure chemical resistance. The display board 10 may be bent at a predetermined curvature before or after letters are carved. The display board 10 thus formed is then attached to the connector portion 9.

To the control section 2, equipped is a display board 11 indicating a type of the endoscope 1. To ensure chemical resistance, the display board 11 is preferably made of a polyphenylene ether resin such as noryl (trade name) or a polysulfone resin having a high chemical resistance. The display can be made by printing letters on the board or applying color to depressed portions for letters which have been made deeper than the level of the board. As a painting material for use in printing or coloring, an acrylic or an epoxy paint is preferably used since they are highly chemical resistant. Alternatively, the display can be made by laser marking.

Figure 2:
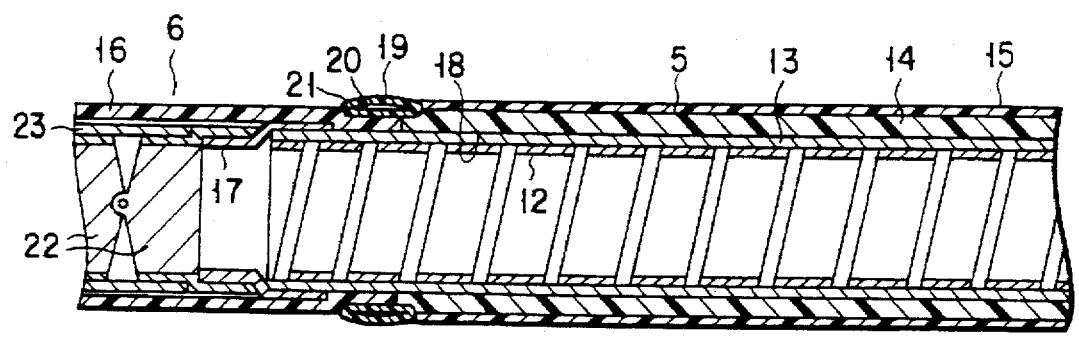
FIG. 2 is a sectional view showing a structure of a flexible tubular body with a bending section, of the endoscope shown in FIG. 1.

FIG. 2 is a sectional view showing a structure of the flexible tube 5 with the bending section 6, of the insertion tubular section 3 in the endoscope 1 explained above.

The flexible tube 5 comprises a flex (spiral tube) 12, a braid (network tube) 13, flexible sheath 14, and coating layer 15. The braid 13, flexible sheath 14, and the coating layer 15 are layered around the flex 12 in the order mentioned. The bending section 6 is connected to an end of the flexible tube 5, the periphery of the bending section 6 is covered with sheath 16.

The bending section 6 is connected to the flexible tube 5 as follows: The bending section 6 is externally inserted into a connecting mouthpiece 17 until the end of the bending section 6 contacts the end of sheath 14. Then, string 19 for tight binding is wound up to the end portion of sheath 16 of the bending section 6 which is inserted into the side of exposed braid 13. The tight-binding string 19 is also wound up to the narrow-diameter portion 18 of the sheath 14 of the flexible tube 5. Thereafter, an adhesive agent 20 is applied to the portion wound up with the string 19. On the layer of an adhesive agent 20, a coating layer 21 is further formed to ensure watertight fixation.

It is preferred to form the coating layer 21 onto the layer of the adhesive agent 20 after it is completely dried. If so, smooth surface can be obtained since projections and depressions formed by the tight-binding string 19 itself can be covered. To make the surface of the coating layer 21 smoother, the following method may be applied. In the first place, the tight-binding string 19 is fixed with a highly viscous adhesive agent and subsequently a low viscous adhesive agent is applied thereon. After completion of drying, a coating agent is further applied thereon and dried. In this way, the connecting section may be formed in a three-layered structure.

In FIG. 2, reference numeral 22 indicates a plurality of jointing rings which allow the adjoining structure members constituting the bending section 6 to connect to each other so as to revolve universally. Reference numeral 23 is a braid (network tube) of the bending section 6.

In the present invention, a coating layer of aliphatic resins is employed as the coating layer 15 which is the outer surface of the flexible tube 5 having the aforementioned structure, and also employed as the coating layer 21 formed on the layer of the adhesive agent 20. Furthermore, the coating layer of aliphatic resins may be formed on the outer surface of the sheath 16 of the bending section.

The coating layer 15 of the flexible tube 5 is formed on the surface of the sheath 14 in the above; however, the present invention should not be restricted thereto. For example, the sheath 14 itself may be formed of the coating layer of aliphatic resins. In other words, the coating layer of aliphatic resins can be directly formed on the surface of the braid 13. In the same manner, on the surface of braid 23 of the bending section 6, the coating layer of aliphatic resins can be directly formed.

Moreover, the coating layer of aliphatic resins may be formed on the outer face of the light guide cable 4. In this case, it is preferred that the coating layer of aliphatic resins have thickness in the range from 0.005 to 0.1 mm.

The coating layer of aliphatic resins used herein can be formed by using an epoxy coating agent, an acrylic coating agent or an urethane coating agent.

As the epoxy coating agent, aliphatic diglycidyl ether or the like may be used. Example of the acrylic coating agent include methacrylate hydroxyethylacrylate and the like. In view of wear resistance and flexibility, the urethane coating agent is particularly preferable. Hereinbelow, the aliphatic urethane coating agent will be explained in detail.

The aliphatic urethane coating agents are classified into one liquid type and two liquids type. By using these liquids as instructed below, a coating layer excellent in chemical resistance will be obtained.

First, we will explain the case where the aliphatic coating agents of one liquid type is used. Of the aliphatic urethane coating agents of one liquid type, a polyurethane painting of a wet-cured type is particularly preferable. In this case, a coating layer is formed as follows: An aliphatic diisocyanate is coupled with a dihydric or a trihydric alcohol to produce an aliphatic prepolymer having a crosslinked structure. This aliphatic prepolymer is responsible for forming a coating layer.

Examples of the aliphatic diisocyanate include hexamethylene diisocyanate, isophorone diisocyanate, lysine diisocyanate and the like. Hexamethylene diisocyanate is particularly preferable.

Specific examples of the dihydric or trihydric alcohol include trimethylol propane, glycerin, ethylene glycol and the like. Preferably, trimethylol propane is used.

When the aliphatic prepolymer containing the aforementioned components is coated on the surface of the tubular body, a free NCO group is reacted with water in the air to form an urea bond as shown below. The urea bond thus obtained is then reacted with isocyanate to form a biuret compound, which is responsible for forming a coating film having a high molecular network structure.

Wherein R is an alkyl group or an alicyclic group.

To improve the curing and drying characteristics of the aliphatic polyisocyanate, it is preferred to use a curing accelerating catalyst made of an acid, a base or various metal compounds. The curing accelerating catalyst is contained in an amount of 1 to 15 parts by weight, regarding the amount of prepolymer as 100 parts by weight. Curing may be further accelerated if the curing reaction is carried out at a temperature from 50° to 150° C.

To improve smoothness of the coating surface, it is preferred to contain about 0.1 to 30% of a friction reducing material in the curing accelerating catalyst. As the friction reducing material, silicone or fluororesin is preferably used.

Hereinbelow, we will explain the case in which the aliphatic urethane coating agent of two liquids type is used. As the aliphatic urethane coating agent of two liquids type, painting containing a polyurethane resin of a polyol curing type is particularly preferable. In this case, a polyol prepolymer is first mixed with a polyisocyanate prepolymer to prepare a mixture solution. Subsequently, the mixture solution is applied onto the surface of the tubular body and allowed to dry. In this manner, the coating layer is formed. The polyisocyanate prepolymer used herein is prepared by reacting a polyhydric alcohol with an excessive amount of aliphatic diisocyanate.

As the polyol, use may be made of polyether polyol, polyester polyol, acrylic polyol, epoxy polyol and the like. Examples of diisocyanate used herein hexamethylene diisocyanate, xylylene diisocyanate, lysine diisocyanate, and the like. Examples of the polyhydric alcohol include trimethylol propane, glycerin, ethylene glycol and the like.

When the mixture solution containing the aforementioned components is applied onto the surface of a tubular body, a coating layer is formed through the following reaction.

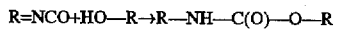

$$R\text{—}NCO + HO\text{—}R \rightarrow R\text{—}NH\text{—}C(O)\text{—}O\text{—}R$$

wherein R is an alkyl group or an alicyclic group.

The sheath, namely, an underlying layer to be coated with the aforementioned coating layer of aliphatic resins, is preferably formed of a polymer. As the polymer, use may be made of a thermoplastic elastomer and a non-thermoplastic elastomer. Preferably, the thermoplastic elastomer is used. Examples of the thermoplastic elastomer include a polyurethane thermoplastic elastomer and a polyester thermoplastic elastomer. In particular, an aliphatic polyurethane thermoplastic elastomer is preferably used.

The sheath of the insertion section is formed by using the aforementioned elastomer as follows: To the underlying layer of the insertion section, an elastomer in a molten state is applied by means of an extruding machine. As an alternative way, the elastomer is dissolved in a solvent such as THF (tetrahydrofuran) and DMF (N,N-dimethyl-formamide) to prepare a liquid-state elastomer and then applied to the underlying layer of the insertion section by dipping. Moreover, the entire sheath layer can be formed of such an aliphatic elastomer.

EXAMPLE 1

On the surface of the flexible tube 5 shown in FIGS. 1 and 2, an aliphatic coating agent was applied and allowed to dry hard, thereby forming a coating layer. The aliphatic coating agent used herein contains 100 parts by weight of aliphatic urethane prepolymer and 10 parts by weight of a curing accelerating catalyst containing 10 wt % of silicone. The prepolymer was dried hard for 10 hours in a constant temperature bath of 60° C. After the curing, the cured product may be dipped in alcohol and radiated with an ultraviolet ray.

For comparison, a coating layer is formed onto the surface of the insertion section of another endoscope in the same manner as in the above except that an aromatic coating agent comprising an aromatic urethane prepolymer was used.

The inserting portions of two endoscopes thus coated were immersed in an oxidative disinfectant. The immersion was repeated 100 times and 300 times for 15 minutes per time. As the disinfectant, highly concentrated acetic acid was used. Thereafter, the dynamic frictional resistance and change in the appearance of the coating layer were checked.

The dynamic frictional resistance was measured by using a friction meter in accordance with the following procedures. First, the surface of a sample was cleaned with ethyl alcohol and fixed on a sample holder of the friction meter with the measuring surface up. On the measuring surface, a contactor formed of PTFE was set so as not to load on the sample. Subsequently, while 100 g of weight was placed immediately on the contactor in order to directly load on the measuring surface of the sample, the sample holder was moved in the direction perpendicular to loading direction at a rate of 50 mm/min. Load in tension at this moment was measured by a load cell of the friction meter, thereby determining dynamic friction drag of the sample. The results thus obtained are shown in Table 1, together with change in the appearance of the samples.

TABLE 1

| | Change in Smoothness and Appearance after Dipping in a Peroxide Disinfectant | | | |
|---|---|---|---|---|
| | Aliphatic series coating agent | | Aromatic series coating agent | |
| | Smoothness (dynamic friction drag) | Appearance | Smoothness (dynamic friction drag) | Appearance |
| Initial | 0.17 | — | 0.33 | — |
| 100 times | 0.18 | No Change | 0.41 | Sticky and yellowish |
| 300 times | 0.15 | " | 0.37 | More sticky and yellowish |

As is apparent from Table 1, when the aliphatic urethane coating agent is used, surface smoothness is satisfactory in the initial time. Even after the samples are immersed in the aliphatic urethane coating agent 100 times and 300 times, no change was observed in the surface smoothness and appearance.

In contrast, when the aromatic coating agent is used, the initial dynamic frictional resistance is as high as 0.33. From this, it is clear that the surface smoothness of the sample coated with the aromatic coating is extremely lower than that of the present invention using the aliphatic coating agent. In the case of the sample coated with the aromatic coating agent, the sample obtained after 100 times immersion exhibited deterioration in the surface smoothness and a sticky and yellowish surface appearance. In the sample obtained after 300 time immersion, the surface became much sticker, so that the sample was no longer in a usable condition.

As evidenced above in this embodiment, an endoscope with an insertion section having a smooth surface and improved chemical resistance to an oxidative disinfectant can be successfully obtained.

EXAMPLE 2

In FIG. 2, on the outer surface of the flexible tube 5, the aliphatic urethane coating layer 15 was formed in the same manner as in Example 1. On the other hand, to the outer surface of the adhesive layer 20, an epoxy coating agent was applied to form the coating layer 21.

Onto the coating layer 21, the tight-binding string 19 may be fixed. Alternatively, after the adhesive agent is applied to the tight-binding string 19 and dried, the coating layer 21 may be formed thereon. Furthermore, after two types of adhesive agents different in viscosity are successively applied and dried, the coating layer 21 having three-layered structure may be formed thereon.

The insertion section of an endoscope, coated as mentioned above, was immersed in an oxidative disinfectant in the same manner as in Example 1. Thereafter, the dynamic frictional resistance and appearance of the coating layer were checked. As a result, an endoscope with an insertion section having excellent surface smoothness and improved resistance to the oxidative disinfectant was successively obtained in the same manner as in Example 1.

EXAMPLE 3

In FIG. 2, on the outer surface of the flexible tube 5, the aliphatic urethane coating layer 15 was formed in the same manner as in Example 1. On the other hand, to the outermost surface of the bending section 6, the same epoxy coating agent as that used in Example 2 was applied to form the coating layer 21.

The insertion section of an endoscope, coated as mentioned above, was immersed in an oxidative disinfectant in the same manner as in Example 1. Thereafter, the dynamic frictional resistance and appearance of the coating layer were checked. As a result, an endoscope with an insertion section having excellent surface smoothness and improved resistance to the oxidative disinfectant was successively obtained in the same manner as in Example 1.

In the above examples, we explained the case in which the present invention was applied to the insertion tubular section of a fiber scope as shown in FIG. 1. However, the present invention is not limited thereto. For example, the coating layer of aliphatic resins can be formed on the surface of a tubular portion of a video scope, for transmitting picture images through CCD. Furthermore, the coating layer of aliphatic resins can be formed on the outer surface of a sliding tube which is used as an auxiliary instrument for inserting an endoscope into the large intestine. In short, the coating of aliphatic resins can be applied any surface of members which are exposed to an oxidative disinfectant.

As explained in the foregoing, the present invention provides an endoscope comprising a tubular body having excellent smoothness and excellent resistance to an oxidative disinfectant.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An endoscope comprising a flexible tubular body, wherein at least one portion of said flexible tubular body has a coating layer of aliphatic resins which is formed by applying a coating agent containing an aliphatic prepolymer which is a reaction product of an aliphatic diisocyanate and a polyester polyol, onto the surface of an outermost layer of a sheath made of a polymer material, and curing the coating agent.

2. The endoscope according to claim 1, wherein a tubular body having said coating layer of aliphatic resins is an insertion tubular section comprising a flexible tubular section, a bending section and a connecting section therebetween.

3. The endoscope according to claim 2, wherein said tubular body having said coating layer of aliphatic resins is the flexible tubular section of said insertion tubular section.

4. The endoscope according to claim 2, wherein said tubular body having said coating layer of aliphatic resins is the bending section of said insertion tubular section.

5. The endoscope according to claim 2, wherein the tubular body having said coating layer of aliphatic resins is the connecting section between the flexible tubular section and the bending section of said insertion tubular section.

6. The endoscope according to claim 1, wherein said aliphatic diisocyanate is at least one diisocyanate selected from the group consisting of hexamethylene diisocyanate, xylylene diisocyante and lysine diisocyanate.

7. The endoscope according to claim 1, wherein said coating layer of aliphatic resins further contains a friction reducing material.

8. The endoscope according to claim 7, wherein said friction reducing material is a silicone resin.

9. The endoscope according to claim 7, wherein said friction reducing material is a fluororesin.

10. The endoscope according to claim 1, wherein the tubular body having said coating layer of aliphatic resins is a light guide cable.

11. The endoscope according to claim 1, wherein said polymer material is an elastomer.

12. The endoscope according to claim 11, wherein said elastomer is a thermoplastic elastomer.

13. The endoscope according to claim 12, wherein said thermoplastic elastomer is a polyurethane thermoplastic elastomer.

14. The endoscope according to claim 13, wherein said polyurethane thermoplastic elastomer is an aliphatic polyurethane thermoplastic elastomer.

15. The endoscope according to claim 12, wherein said thermoplastic elastomer is a polyester thermoplastic elastomer.

16. The endoscope according to claim 11, wherein said elastomer is a non-thermoplastic elastomer.

17. The endoscope according to claim 11, wherein said tubular body having said coating layer of aliphatic resins is an insertion tubular section, and said elastomer is applied to an underlying layer of said insertion tubular section by means of an extruding machine in a molten state.

18. The endoscope according to claim 11, wherein said tubular body having said coating layer of aliphatic resins is an insertion tubular section, and said elastomer is dissolved in a solvent selected from the group consisting of tetrahydrofuran and N,N-dimethyl-formamide to prepare a liquid-state elastomer and then applied to an underlying layer of said insertion tubular section by dipping.

* * * * *